United States Patent
Asada

(10) Patent No.: US 8,131,382 B2
(45) Date of Patent: Mar. 6, 2012

(54) SAMPLE PROCESSING APPARATUS AND DATA PROCESSING APPARATUS

(75) Inventor: Shoichiro Asada, Hyogo (JP)

(73) Assignee: Sysmex Corporation, Kobe (JP)

( * ) Notice: Subject to any disclaimer, the term of this patent is extended or adjusted under 35 U.S.C. 154(b) by 765 days.

(21) Appl. No.: 12/286,031

(22) Filed: Sep. 26, 2008

(65) Prior Publication Data

US 2009/0088869 A1 Apr. 2, 2009

(30) Foreign Application Priority Data

Sep. 27, 2007 (JP) .................................. 2007-252217

(51) Int. Cl.
*G06F 19/00* (2011.01)
(52) U.S. Cl. ................................ 700/3; 700/9; 709/208
(58) Field of Classification Search .................. 700/3, 9; 709/208
See application file for complete search history.

(56) References Cited

U.S. PATENT DOCUMENTS 5,772,963 A * 6/1998 Cantatore et al. ............... 422/67
(Continued)

*Primary Examiner* — Michael D Masinick
(74) *Attorney, Agent, or Firm* — Brinks Hofer Gilson & Lione

(57) ABSTRACT

A sample processing apparatus, comprising: a sample processing unit for processing a sample, wherein the sample processing unit comprises an operating device for processing a sample, a drive circuit for driving the operating device, and a first communication part which is configured so as to be capable of external communication; and a data processing unit for processing data output from the sample processing unit, wherein the data processing unit comprises a processor for generating control data for controlling the operating device, and a second communication part which is configured so as to be capable of communicating with the first communication part for transmitting the control data generated by the processor to the first communication part, wherein the drive circuit is configured so as to drive the operating device based on the control data received by the first communication part, is disclosed. A data processing apparatus is also disclosed.

20 Claims, 6 Drawing Sheets

U.S. PATENT DOCUMENTS

| | | | |
|---|---|---|---|
| 5,988,857 A * | 11/1999 | Ozawa et al. | 700/213 |
| 6,444,171 B1 * | 9/2002 | Sakazume et al. | 422/65 |
| 6,780,617 B2 * | 8/2004 | Chen | 435/91.2 |
| 7,788,669 B2 * | 8/2010 | England et al. | 718/104 |
| 2004/0230794 A1 * | 11/2004 | England et al. | 713/164 |
| 2006/0277330 A1 * | 12/2006 | Diepstraten et al. | 710/40 |
| 2009/0011417 A1 * | 1/2009 | Maltezos et al. | 435/6 |

* cited by examiner

| IRQL | Name |
|---|---|
| 31 | HIGH LEVEL |
| 30 | POWER LEVEL |
| 29 | IPI LEVEL |
| 28 | CLOCK2 LEVEL |
| 28 | CLOCK1 LEVEL |
| 27 | PROFILE LEVEL |
|  | DIRQL |
|  | ... |
|  |  |
| 2 | DISPATCH LEVEL |
| 1 | APC LEVEL |
| 0 | PASSIVE LEVEL |

FIG.3

SAMPLE PROCESSING APPARATUS AND DATA PROCESSING APPARATUS

RELATED APPLICATIONS

This application claims priority under 35 U.S.C. §119 to Japanese Patent Application No. JP2007-252217 filed Sep. 27, 2007, the entire content of which is hereby incorporated by reference.

FIELD OF THE INVENTION

The present invention relates to a sample processing apparatus and data processing apparatus, for example a sample processing apparatus and data processing apparatus for measuring a sample.

BACKGROUND

Conventional sample processing apparatus and data processing apparatus for measuring a sample are known (for example, refer to Japanese Laid-Open Patent No. 10-197509).

The liquid chromatographic analyzer disclosed in Japanese Laid-Open Patent No. 10-197509 is provided with an analyzing part for analyzing a target sample, and a data processing part for obtaining analysis results by performing an analysis process on the data obtained by the analyzing part.

The analyzing part is provided with a controller for controlling the operation of the analyzing part. The data processing part is a personal computer which is configured so as to perform analysis processing of data obtained by the analyzing part.

There are problems with the liquid chromatographic analyzer disclosed in Japanese Laid-Open Patent No. 10-197509, however, in that the structure of the apparatus is complicated by the provision of individual controllers for the analyzing part and data processing part, thereby increasing manufacturing costs.

SUMMARY OF THE INVENTION

The scope of the present invention is defined solely by the appended claims, and is not affected to any degree by the statements within this summary.

A first aspect of the present invention is a sample processing apparatus, comprising: a sample processing unit for processing a sample, wherein the sample processing unit comprises an operating device for processing a sample, a drive circuit for driving the operating device, and a first communication part which is configured so as to be capable of external communication; and a data processing unit for processing data output from the sample processing unit, wherein the data processing unit comprises a processor for generating control data for controlling the operating device, and a second communication part which is configured so as to be capable of communicating with the first communication part for transmitting the control data generated by the processor to the first communication part, wherein the drive circuit is configured so as to drive the operating device based on the control data received by the first communication part.

A second aspect of the present invention is a data processing apparatus, comprising: a memory for storing a control program for controlling an operating device of a sample processing apparatus for processing a sample; a processor for executing a control program stored in the memory, and generating control data for controlling the operating device; and a communication part which is connected so as to be capable of communication with the sample processing apparatus, for transmitting the control data generated by the processor to the sample processing apparatus.

A third aspect of the present invention is a sample processing apparatus, comprising: a sample processing unit for processing a sample; and a data processing unit for processing data output from the sample processing unit, wherein the sample processing unit includes a memory under control of a processor, the memory storing a first program for generating control data controlling the sample processing unit, a second program for processing the data output from the sample processing unit, and an operating system which determines priority of program execution, wherein the first program and the second program are stored in the memory such that the first program is executed by interrupting execution of the second program under control of the operating system.

BRIEF DESCRIPTION OF THE DRAWINGS

FIG. 3 illustrates the structure of the operating system (OS) used in the blood analyzer of the embodiment shown in FIG. 1;

DETAILED DESCRIPTION OF THE PREFERRED EMBODIMENTS

The preferred embodiments of the present invention will be described hereinafter with reference to the drawings.

Figure 1:
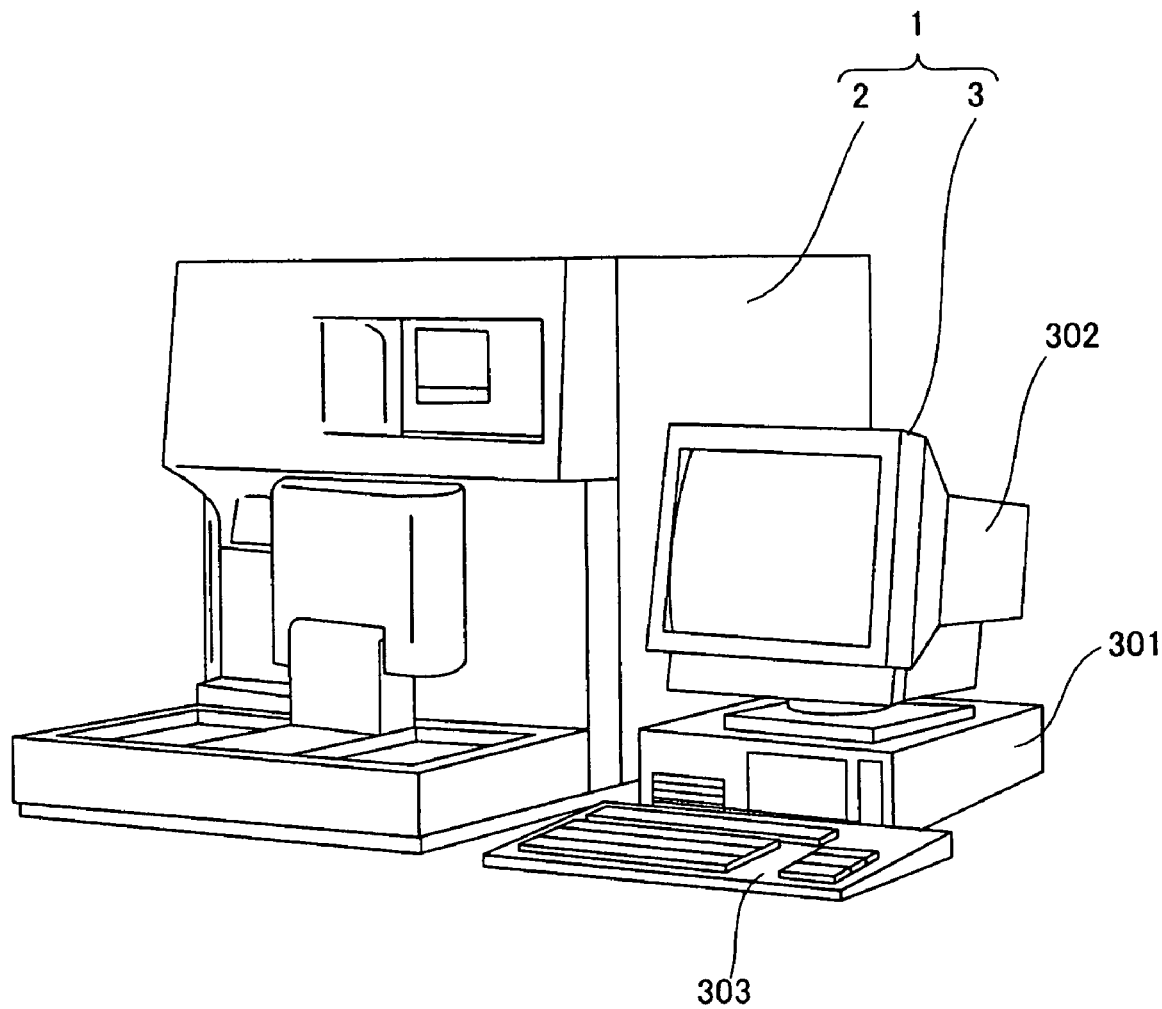
FIG. 1 is a perspective view showing the general structure of an embodiment of the blood analyzer of the present invention.
Figure 2:
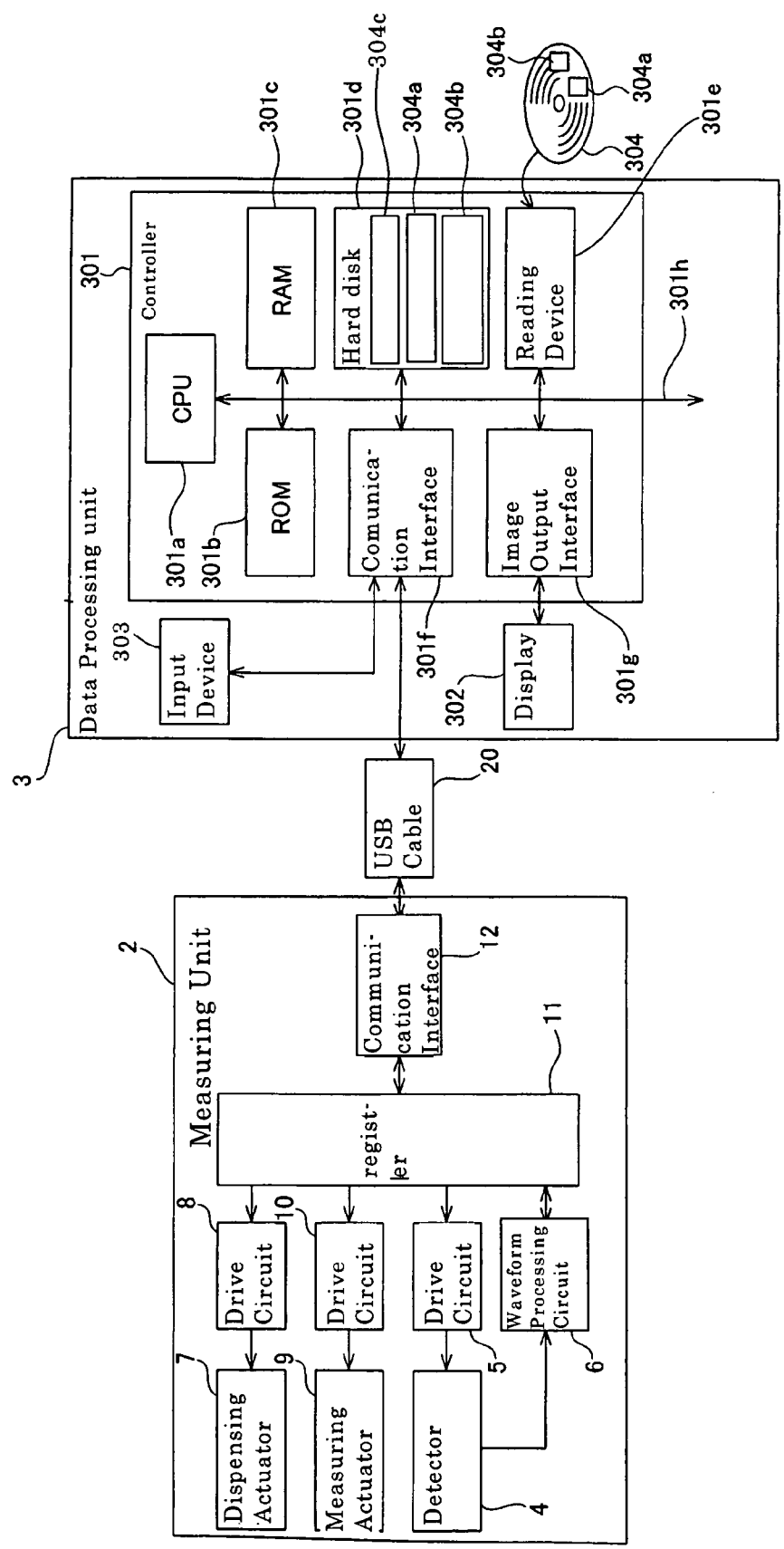
FIG. 2 is a block diagram showing the structure of the measuring unit and data processing unit of the embodiment of the present invention.

FIG. 1 is a perspective view showing the general structure of an embodiment of the blood analyzer of the present invention. FIG. 2 is a block diagram showing the structure of the measuring unit and data processing unit of the embodiment of the present invention. FIG. 3 illustrates the structure of the OS used in the blood analyzer of the embodiment shown in FIG. 1. The general structure of an embodiment of the blood analyzer 1 of the present invention is described below with reference to FIGS. 1 through 3.

The blood analyzer 1 of the embodiment of the present invention is an apparatus which analyzes the blood cells in blood by irradiating each particle with laser light as the particles such as cells and hemocytes are directed through a flow cell, and then detecting the scattered light and fluorescent light from each particle.

As shown in FIG. 1, the blood analyzer 1 is configured by a measuring unit 2 which has the function of measuring the sample blood, and a data processing unit 3 for processing the measurement results output from the measuring unit to obtain analysis results. As shown in FIG. 2, the measuring unit 2 is provided with a blood cell detector 4, a drive circuit 5 for driving (operating) the detector 4, a waveform processing circuit 6 for performing waveform processing of the signals output from the detector 4, a dispensing actuator 7 which is actuated when dispensing a sample, a drive circuit 8 for driving the dispensing actuator 7, a measuring actuator 9 which outputs measurement data, and a drive circuit 10 for driving the measuring actuator 9.

The detector 4 is configured as an optical detector. Specifically, the detector 4 is configured so as to detect cells and particles such as blood cells and the like in blood by flow cytometry. Note that flow cytometry is a method for measuring physical properties and chemical properties of cells and other biological particles by passing the cells and other biological particles through a narrow passage. The detector 4 is configured so as to detect the forward scattered light, side scattered light, and side fluorescent light emitted from the blood cells which are irradiated by laser light.

Specifically, the drive circuit 5 is connected to the detector 4 and the drive circuit 5 is also connected to a register 11. The detector 4 is configured so that the drive circuit 5 operates and drives the laser light oscillation and the like by outputting signals according to the control data which is to be described layer that is stored in the register 11.

The detector 4 is also configured to be capable of converting the respectively detected forward scattered light, side scattered light, and side fluorescent light from optical signals to electrical signals. Furthermore, the waveform processing circuit 6 is connected to the detector 4, and the various electrical signals which have been converted from optical signals are transmitted to the waveform processing circuit 6. The waveform processing circuit 6 is configured so as to be capable of then amplifying the electrical signals of the forward scattered light, side scattered light, and side fluorescent light, and performing waveform processing of the amplified electrical signals of the side scattered light. The waveform processing circuit 6 is also connected to the register 11, and is configured so as to store the electrical signals processed by the waveform processing circuit 6 in the register 11.

The drive circuit 8 is connected to the dispensing actuator 7, and the drive circuit 10 is connected to the measuring actuator 9. The drive circuits 8 and 10 are respectively connected to the register 11, and the dispensing actuator 7 and the measuring actuator 9 are configured so as to be driven according to the control signals output by the drive circuit 8 and drive circuit 10 according to the control data stored in the register 11 which will be described later.

A communication interface 12 is also connected to the register 11. The communication interface 12 is a USB serial interface, and is configured so as to be connectable by a USB cable to a communication interface 301*f* of the data processing unit 3 which will be described later. Data is thus transmitted and received to/from the data processing unit 3.

As shown in FIG. 1, the data processing unit 3 is configured by a personal computer (PC), and includes a controller 301 configured by a CPU, RAM, ROM and the like, a display part 302, and an input device 303. The display part 302 is provided to display the analysis results obtained by processing the data of the digital signals received from the measuring unit 2.

The structure of the data processing unit 3 is described below. As shown in FIG. 2, the data processing unit 3 is a computer which is mainly configured by a controller 301, display part 302, and input device 303. The controller 301 is mainly configured by a CPU 301*a* (for example, a Celeron 2,000 MHz), ROM 301*b*, RAM 301*c*, (for example, 512 MB RAM), hard disk 301*d*, reading device 301*e*, communication interface 301*f*, and image output interface 301*g*. The a CPU 301*a*, ROM 301*b*, RAM 301*c*, hard disk 301*d*, reading device 301*e*, communication interface 301*f*, and image output interface 301*g* are connected by a bus 301*h*.

The CPU 301*a* is capable of executing computer programs stored in the ROM 301*b*, and computer programs loaded in the RAM 301*c*. The computer functions as the data processing unit 3 when the CPU 301*a* executes an application program 304*a* and control program 304*b* which will be described later. In the present embodiment, the CPU 301*a* is configured so as to execute at predetermined time intervals (on average approximately every 100 msec) a process for generating control data (control signals) for controlling the dispensing actuator 7, and measuring actuator 9, and detector 4 of the measuring unit 2.

The ROM 110*b* is configured by a mask ROM, PROM, EPROM, EEPROM or the like, and stores computer programs executed by the CPU 301*a* and data and the like used in conjunction therewith.

The RAM 301*c* is configured by SRAM, DRAM or the like. The RAM 301*c* is used when reading the computer programs recorded in the ROM 301*b* and stored on the hard drive 301*d*. The RAM 301*c* is also used as a work area of the CPU 301*a* when the computer programs are being executed.

The hard drive 301*d* contains various installed computer programs to be executed by the CPU 301*a* such as an operating system and application programs and the like, as well as data used in the execution of these computer programs. The application program which is to be described later is stored on the hard disk 401*d* together with the control program 304*b* and operating system 304*c*.

The reading device 301*e* is configured by a floppy disk drive, CD-ROM drive, DVD-ROM drive or the like, and is capable of reading the computer programs and data stored on a portable recording medium 304. The portable recording medium 304 stores the application program 304*a* and control program 304*b* for realizing the functions the data processing unit in a computer, and the application 304*a* and the control program 304*b* are read from the portable recording medium 304 by the computer, which installs the application program 304*a* and the control program 304*b* on the hard disk 301*d*.

The application program 304*a* and control program 304*b* are not only provided through the portable recording medium 304 inasmuch as the application program 304*a* and control program 304*b* may also be provided from an external device which is connected to the computer over an electric communication line so as to be capable of communication by this electric communication line (whether wire line or wireless). For example, when the application program 304*a* and the control program 304*b* are stored on the hard disk of a server computer on the Internet, the computer may access the server computer and download the application program 304*a* and control program 304*b*, which are then installed on the hard disk 301*d*.

An operating system (OS) 304*c* which provides a graphical user interface environment, for example, Windows (registered trademark) or the like, a product of Microsoft Corporation, USA, is installed on the hard disk 301*d*. In the following description, the application program 304*a* and the control program 304*b* operate on this operating system 304*c* in the present embodiment. The operating system 304*c* determines the priority for executing the programs between the application program 304*a* and the control program 304*b*, and executes these programs according to the determined priority.

The communication interface 301*f* is a USB serial interface similar to the previously mentioned communication interface 12. The input device 303 (refer to FIG. 1) which is configured by a mouse and keyboard is connected to the communication interface 301*f*, and a user can input data to the data processing unit 3 by using the input device 303. In the present embodiment, the communication interface 301f of the data processing unit 3 and the communication interface 12 of the measuring unit 2 are respectively configured so as to transmit and receive control data (control signals) which are generated based on the control program 304b by interrupt transfer, which is a transfer method that guarantees the data transfer time. The measuring unit 2 and the data processing unit 3 of the present embodiment are thus configured so that the control data (control signals) generated by the CPU 301 of the data processing unit 3 are received by the measuring unit 2 within a fixed time. Note that interrupt transfer is transfer method for reliably transferring a predetermined amount of data (for example, 1,000 bytes) at predetermined time intervals (for example, 125 msec).

The image output interface 301g is connected to the display part 302 which is configured by an LCD, CRT or the like, and outputs image signals according to the image data received from the CPU 301a to the display part 302. The display part 302 is configured so as to display an image (screen) based on the input image signals.

In the present embodiment, the application program 304a which is installed on the hard disk 301d of the controller 301 of the data processing unit 3 is configured so as to measure the amount of blood cells of a measurement sample using the forward scattered light, side scattered light, and side fluorescent light (digital signal data) received from the communication interface 12 of the measuring unit 2, and process the measurement data. The control program 304b which is installed on the hard disk 301d generates control data (control signals) for controlling the drive circuits 5, 8, and 10, and the waveform processing circuit 6, and the generated control data are transmitted to the measuring unit 2 through a USB gate 20 which is connected to the communication interface 301f. The transmitted control data is written to (stored in) the register 11 which is connected to the communication interface 12. It is thus possible to control the measuring unit 2, and further possible to drive and operate the dispensing actuator 7 and the measuring actuator 9, and detector 4 of the measuring unit 2 based on the control data generated by the CPU 301a of the data processing unit without providing a microprocessor such as a CPU or the like in the measuring unit 2. The control program 304b is configured so as to control the operation of other devices in addition to the measuring unit 2 as well as the dispensing actuator 7, measuring actuator 9, and detector 4 of the measuring unit 2. Note that the control data includes, for example, data such as the amount of drive and drive timing and the like of the stepping motor included in the dispensing actuator 7 when controlling the dispensing actuator.

In the present embodiment, the application program 304a which is a program for processing measurement data is configured so as to be executable at the user level of the operating system 304c, that is, Windows (registered trademark), and the control program 304b which is a program for controlling the drive circuits 5, 8, and 10 is configured so as to be executable at the kernel level of the highest priority process rather than at the user level of Windows (registered trademark). That is, the application program 304a is stored on the hard disk 301d so as to be executable at the user level of Windows, and the control program 304b is stored on the hard disk 301d so as to be executable at the kernel level of Windows.

Specifically, a plurality of interrupt request levels (IRQL) are provided in Windows (registered trademark), and the IRQL have a hierarchy of 0 to 31, as shown in FIG. 3, The process performed at the hierarchical level with the highest IRQL number is executed preferentially over processes at hierarchical levels with lower numbers. Even when a process is being performed at a low hierarchical level (low level) and a process is to be performed at a hierarchical level with a high IRQL number (high level), the process being performed at the low level is interrupted and the high level process is performed. The application program 304a which is a program for processing the measurement data of the blood analyzer 1 of the present embodiment is configured so as to execute at the PASSIVE_LEVEL (user level) in FIG. 3, and the control program 304b which is a program for controlling the drive circuits 5 8, and 10 of the measuring unit 2 is configured so as to execute at the DISPATCH_LEVEL (kernel level) in FIG. 3. Note that the processes which are performed at levels higher than the DISPATCH_LEVEL in FIG. 3 are referred to as hardware interrupts, and a hardware interrupt may be executed a plurality of times during the operation process performed by the CPU 301a.

In the present embodiment, the CPU 301a is configured so as to execute at predetermined time intervals (on average approximately every 100 msec) a process for generating control data (control signals) for controlling the dispensing actuator 7, measuring actuator 9, and detector 4 of the measuring unit 2.

Figure 4:
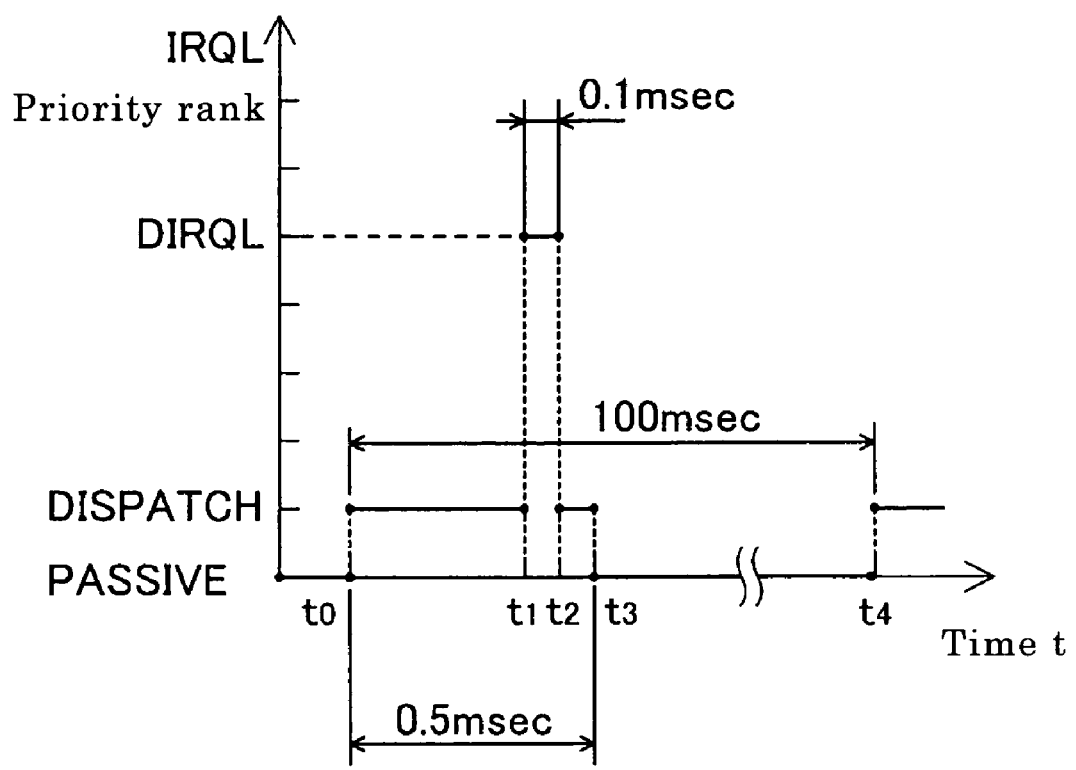
FIG. 4 is a timing chart illustrating the CPU operation time of the blood analyzer of the embodiment shown in FIG. 1.

FIG. 4 is a timing chart illustrating the CPU operation time of the blood analyzer of the embodiment shown in FIG. 1. The timing chart shows the time on the horizontal axis, and on the vertical axis shows the height of the priority rank of the IRQL shown in FIG. 3. Examples of the processing method are described below in the cases when the CPU 301a executes the application program 304a and the control program 304b.

First, the CPU 301 a executes the application program 304a at the PASSIVE_LEVEL, and at time t0 starts the process of generating control data by the control program at the DISPATCH_LEVEL, as shown in FIG. 4. In this case the CPU 301a interrupts the process of the PASSIVE_LEVEL application program 304a during the processing of the control program 304b because the DISPATCH_LEVEL control program 304b is processed preferentially.

When the CPU 301a is executing the DISPATCH_LEVEL control process 304b, a hardware interrupt is raised by DIRQL at time t1. In this case the CPU 301a interrupts the process of the DISPATCH_LEVEL control program 304b while processing the hardware interrupt because the DIRQL hardware interrupt is processed preferentially.

Thereafter, at time t2 the DIRQL hardware interrupt ends. The process of the DISPATCH_LEVEL control program 304b is restarted in conjunction with the end of the hardware interrupt. In this case the CPU 301a does not restart the process of the PASSIVE_LEVEL application program 304a during the processing of the control program 304b because the DISPATCH_LEVEL control program 304b is processed preferentially.

Thereafter, at time t3 the process of the DISPATCH_LEVEL control program 304b ends. Then the process of the PASSIVE_LEVEL application program 304a is restarted in conjunction with the end of the process of the control program 304b.

At time t4 which is approximately 100 msec from time t0 the process of the DISPATCH_LEVEL control program 304b is restarted to generate control data, and the operation identical to the end of the processes of the PASSIVE_LEVEL application program 304a and the DISPATCH_LEVEL program 304b is repeated.

Note that the time interval (t3-t0) between the time t0 when the process of the control program 304b is started to generate control data and the time t3 when the process for generating control data ends is approximately 0.5 msec when using a 2,000 MHz Celeron processor with 512 MB of RAM, and approximately 0.5% of the time interval (t4-t0: approximately 100 msec) until the process of the control program 304b for generating control data is restarted. The time interval (t2-t1) between the time t1 when the hardware interrupt starts to the time t2 when the hardware interrupt ends is generally approximately 0.1 msec, so brief as to be normally negligible. That is, the influence of the hardware interrupt and the process of the control program 304b for generating control data on the PASSIVE_LEVEL application program 304a can essentially be ignored. The above numeric values are based on simulation results conducted by the CPU 301a under a load equal to when a blood analyzer is actually used, and are reproducible.

Figure 5:
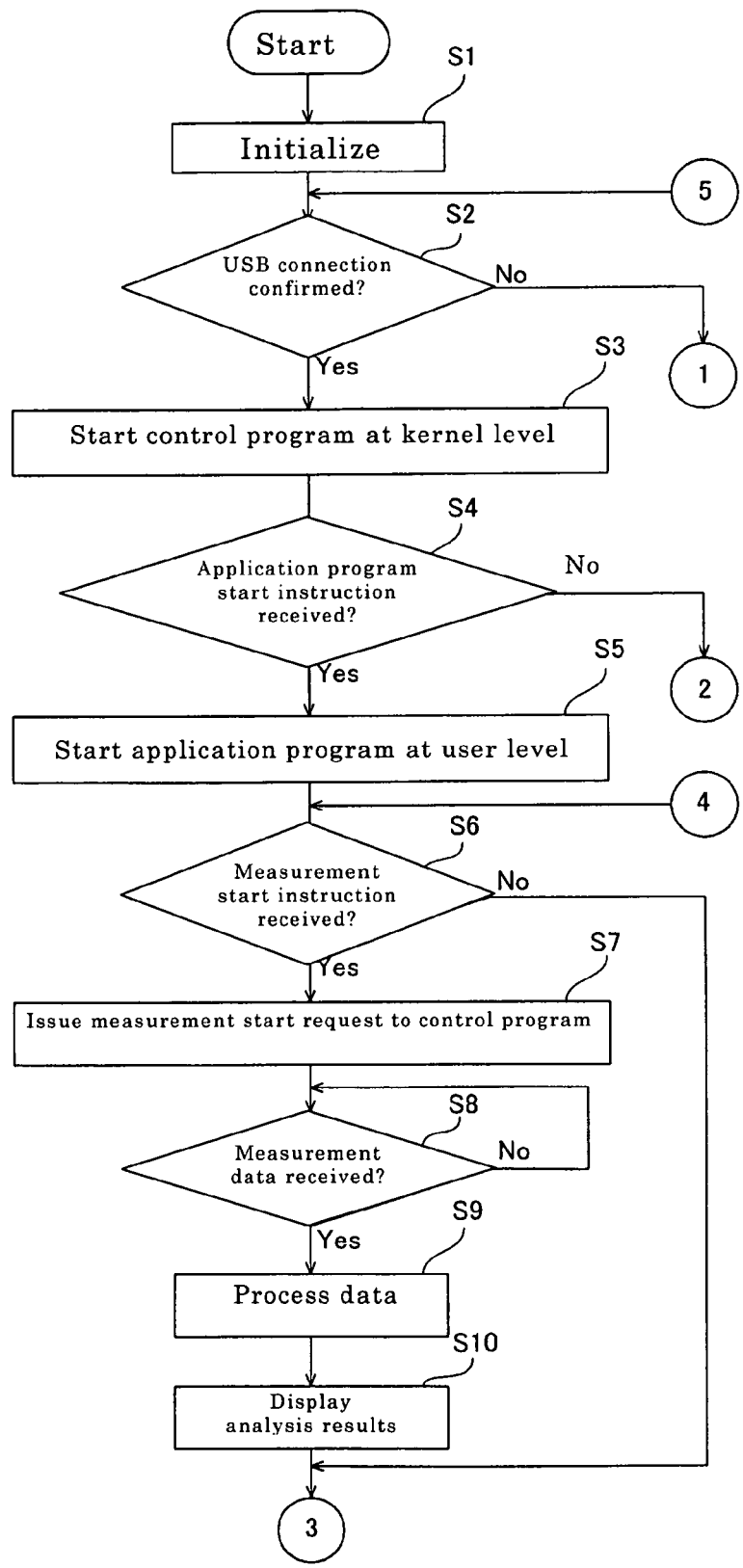
FIG. 5 is a flow chart illustrating the measurement flow and processing flow of the measuring unit and the data processing unit of the blood analyzer of the embodiment shown in FIG. 1.
Figure 6:
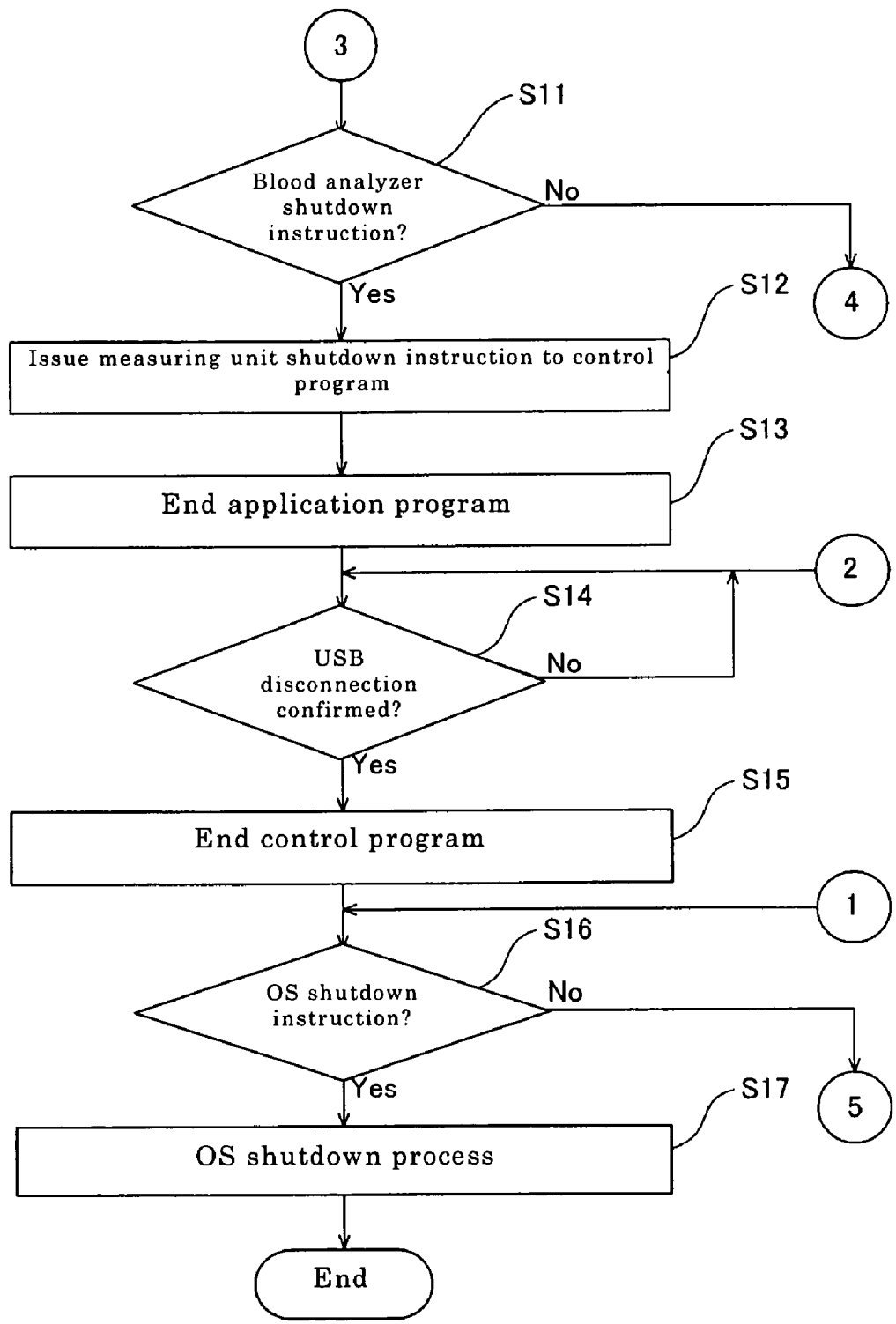
FIG. 6 is a flow chart illustrating the measurement flow and processing flow of the measuring unit and the data processing unit of the blood analyzer of the embodiment shown in FIG. 1.

FIGS. 5 and 6 are flow charts illustrating the measurement flow and processing flow of the measuring unit and the data processing unit of the blood analyzer of the embodiment shown in FIG. 1. The operation when CPU 301a performs the processes of the application program 304a and the control program 304b of the embodiment of the blood analyzer of the present invention is described below with reference to FIGS. 1, 2, 5, and 6.

When a main switch (not shown in the drawing) of the data processing unit 3 is turned on in step S1 of FIG. 5, the CPU 301a (refer to FIG. 2 is initialized and subsequently the Windows (registered trademark) OS of the data processing unit 3 is started.

Then, in step S2 the CPU 301a (refer to FIG. 2) determines whether or not the USB cable 20 is connected to both the communication interface 301f of the data processing unit 3 and the communication interface 12 of the measuring unit 2. When it has been determined in step S2 that the USB cable 20 is not connected to both the communication interface 301f of the data processing unit 3 and the communication interface 12 of the measuring unit 2, the process then moves to step S16 which will be described later. However, when it has been determined that the USB cable 20 is connected to both the communication interface 301f of the data processing unit 3 and the communication interface 12 of the measuring unit 2 in step S2, the process then moves to steep S3.

Thereafter, in step S3 the CPU 301a starts the control program 304b at the DISPATCH_LEVEL of the kernel level, and the process moves to step S4. In step S4 a check is made as to whether or not a start instruction of the application program 304a has been received by selection from the start menu or double clicking on a predetermined icon. When it has been determined that the application program 304a start instruction has been received in step S4, then in step S5 the CPU 301a starts the application program 304a at the PASSIVE_LEVEL of the user level, and the process moves to step S6. When the CPU 301a has determined that the application program 304a start instruction has not been received in step S4, then the process moves to step S14 of FIG. 6 which will be described later.

Then, in step S6 a check is made to determine whether or not a measurement start instruction has been transmitted to the measuring unit 2 through the USB cable 20 by pressing a start switch which is not shown in the drawing provided on the measuring unit 2. When it is not determined that a measurement start instruction has not been transmitted to the data processing unit 3 in step S6, the process moves to step S11 in FIG. 6 which will be described later. When it is determined that a measurement start instruction has been transmitted to the data processing unit 3 in step S6, the process moves to step S7 and a measurement start request for starting the measurement in the measuring unit 2 is issued to the control program 304b by inter-program communication between the application program 304a and the control program 304b. Therefore, the CPU 301a generates control data at approximate 100 msec intervals as previously described based on the control program 304b, the generated control data are written to the register 11 of the measuring unit 2 through the USB cable 20, and the drive circuits 5, 8, and 10 are driven.

Thereafter, the CPU 301a determines whether or not measurement data processed by the waveform processing circuit 6 after detection by the detector 4 of the measuring unit 2 have been received in step S8. When it has been determined that measurement data have not been received in step S8, the process of step S8 is repeated. When it has been determined that measurement data have been received in step S8, the process moves to step S9.

Thereafter, the CPU 301a processes the received measurement data in step S9, then the process moves to step S10. In step S10 the analysis results are displayed on the display part 302, and the process moves to step S11 of FIG. 6.

Thereafter, the CPU 301a determines whether or not a shutdown instruction has been received from the user to shut down the blood analyzer 1 in step S11, as shown in FIG. 6. The user can issue a shutdown instruction to shut down the blood analyzer 1 by clicking a shutdown icon which is not shown in the drawing displayed on the display part 302 of the data processing unit 3, or selecting shutdown from a menu in a display screen of the application program 304a. When the CPU 301a does not determine that a shutdown instruction has been received in step S11, the process returns to the process of step S6 of FIG. 5, and the operations from step S6 to step S11 are thereby repeated. When it has been determined that a blood analyzer 1 shutdown instruction has been received in step S11, the process moves to step S12 and a shutdown request to shut down the measuring unit 2 is issued to the control program 304b by inter-program communication between the application program 304a and the control program 304b. Then, a shutdown operation which includes washing operations and the like is executed for each part of the measuring unit 2, and the power to the measuring unit 2 is subsequently turned off.

Thereafter, in step S13 the CPU 301a ends the application program 304a, and the process moves to step S14. In step S14 a determination is made as to whether or not the connection between the communication interface 301f of the data processing unit 3 and the communication interface 12 of the measuring unit 2 has been disconnected by the USB cable 20. When it is determined in step S14 that the connection between the communication interface 301f of the data processing unit 3 and the communication interface 12 of the measuring unit 2 has not been disconnected, the determination of step S14 is repeated until the connection between the communication interface 301f of the data processing unit 3 and the communication interface 12 of the measuring unit 2 is disconnected. Furthermore, when it has been determined in step S14 that the connection between the communication interface 301f of the data processing unit 3 and the communication interface 12 of the measuring unit 2 has been disconnected, the process moves to step S15 and the CPU 301a ends the control program 304b, and the process moves to step S16.

Thereafter, in step S16 the CPU 301a determines whether or not an OS shutdown instruction has been issued by selecting shutdown from the start menu of Windows (registered trademark) of the data processing unit 3. When it has been determined in step S16 that an OS shutdown instruction has not been issued, the process returns to step S2 of FIG. 5. Furthermore, when it is determined that an OS shutdown instruction has been issued in step S16, the process moves to step S17 and the CPU 301a performs the shutdown process of Windows (registered trademark) of the data processing unit 3, and the process ends.

In the present embodiment described above, the dispensing actuator 7, measuring actuator 9 and detector 4 of the measuring device 2 can be driven without providing a CPU in the measuring device 2 by providing the data processing unit 3 with a CPU 301a for executing at predetermined time intervals (approximately 100 msec) a process for generating control data for controlling the detector 4, dispensing actuator 7, and measuring actuator 9, transmitting the control data generated by the CPU 301a to the measuring unit 2, and configuring the drive circuits 5, 8, and 10 of the measuring unit 2 so as to drive the dispensing actuator 7 and measuring actuator 9, and detector 4 of the measuring unit 2 based on the control data transmitted from the measuring unit 2. The structure of the apparatus is therefore less complex and the manufacturing cost of the apparatus is reduced.

In the present embodiment described above, it is possible to suppress interference with the execution by the CPU 301a of the control program 304b for controlling the drive circuits 5, 8, and 10 at predetermined time intervals in conjunction with the execution by the CPU 301a of the application program 304a for processing measurement data since the control program 304b for controlling the drive circuits 5, 8, and 10 is processed in preference to the application program 304a for processing measurement data by executing the control program 304b for controlling the drive circuits 5, 8, and 10 at the kernel level which has a higher priority than the user level. Therefore, the dispensing actuator 7, measuring actuator 9 and detector 4 of the measuring unit 2 can operate in a stable condition regardless of the condition of the processing of the application program 304a for processing measurement data.

In the present embodiment described above, the dispensing actuator 7, measuring actuator 9, and detector 4 of the measuring unit 2 can operate in a stable condition since the control data generated by the data processing unit 3 are transmitted to the measuring unit 2 within a fixed time by configuring the data processing unit 3 and measuring unit 2 so as to respectively transmit and receive the control data by interrupt transfer.

Although the control data have been described as being transmitted via the communication interfaces 301f and 12 which are USB interfaces using an interrupt transfer in the present embodiment described above, the present invention is not limited to this arrangement inasmuch as the control data may also be transferred by bulk transfer. In the case of a bulk transfer, however, if a USB device such as a USB memory or the like is used, the transfer of the control data may not be accomplished in the 100 msec interval due to the influence of the device. It is therefore desirable that an interrupt transfer is used in order to eliminate this influence.

In the embodiment described above, the drive circuits 5, 8, and 10 can drive the dispensing actuator 7, measuring actuator 9, and detector 4 of the measuring unit 2 based on a plurality of control data stored in the register 11 of the measuring unit 2 without providing a microprocessor (controller) in the measuring unit 2 by configuring the dispensing actuator 7, measuring actuator 9, and detector 4 of the measuring unit 2 so as to be driven based on the control data stored in the register 11.

The embodiment disclosed above is in all aspects an example and not to be construed as limiting in any way. The scope of the present invention is defined by the scope of the claims and not be the description of the embodiment, and includes all modifications within the scope of the claims and the meanings and equivalences therein.

For example, although the present invention is described by way of example of an application to a blood analyzer as an example of a sample analyzer in the embodiment above, the present invention is not limited to this application inasmuch as application may also be made to other sample analyzers such as urine analyzers, blood coagulation measuring apparatuses, immunoanalyzers, gene amplification measuring apparatuses and the like insofar as the sample analyzer is provided with a measuring unit and a data processing unit. Furthermore, the present invention is also applicable to smear sample preparing apparatuses provided with a smear sample preparing unit, and a data processing device for executing data processing such as storing data representing a completed smear in a table form, and which is connected to connected to the smear sample preparing unit.

Although the above embodiment is described by way of example in which the measuring unit and the data processing unit are connected by a USB cable, the present invention is not limited to this arrangement inasmuch as the measuring unit and the data processing unit may also be connected by a PCI bus rather than a USB cable.

Although the above embodiment is described by way of example in which the measuring unit and data processing unit are provided with a USB interface, and respectively connected via a USB cable, the present invention is not limited to this arrangement inasmuch as, for example, the measuring unit and data processing unit may be provided with another communication interface such as IEEE1394 and the like so as to be connected by an appropriate communication interface cable. Furthermore, the measuring unit and data processing unit may also be connected by wireless communication using wireless USB or the like.

Although the above embodiment has been described by way of example in which the control program is configured so as to process via DISPATCH_LEVEL at the kernel level, the present invention is not limited to this arrangement inasmuch as the control program may also be configured so as to process via IRGL of a priority rank other than DISPATCH_LEVEL if the control program processes via IRGL of a priority rank higher than PASSIVE_LEVEL of the user level.

Although the above embodiment has been described by way of example in which the control program is configured so that the CPU executes a process to generate control data at intervals of approximately 100 msec, the present invention is not limited to this arrangement inasmuch as the control program may also be configured so that the CPU executes a process for generating control data at times shorter or longer than 100 msec.

Although the above embodiment has been described by way of example in which the application program and control program are executed by the Windows (registered trademark) OS, the present invention is not limited to this arrangement inasmuch as the application program and control program may also be configured so as to be executed by another OS, such as, for example, Linux or the like, if the OS has a plurality of interrupt request levels.

What is claimed is:

1. A sample processing apparatus, comprising:
   a sample processing unit for processing a sample, wherein the sample processing unit comprises:
   an operating device for processing a sample;
   a drive circuit for driving the operating device; and
   a first communication part which is configured so as to be capable of external communication; and
   a data processing unit for processing data output from the sample processing unit, wherein the data processing unit comprises:

a processor for generating, at fixed time intervals, control data defining a content of operation by the operating device; and a second communication part which is configured so as to be capable of communicating with the first communication part for transmitting the control data generated by the processor to the first communication part, wherein the drive circuit is configured so as to drive the operating device according to the control data received by the first communication part.

2. The sample processing apparatus according to claim 1, wherein the first communication part and second communication part are respectively configured so as to transmit and receive the control data by interrupt transfer.

3. The sample processing apparatus according to claim 1, wherein the data processing unit comprises a memory for storing an operating system, and control program for generating the control data; and the control program is stored in the memory and is executable at a kernel level of the operating system.

4. The sample processing apparatus according to claim, wherein the memory further stores a data processing program for processing the data output from the sample processing unit; and the data processing program is stored in the memory and is executable at a user level of the operating system.

5. The sample processing apparatus according to claim 1, wherein the operating device comprises a first actuator for dispensing a sample, a second actuator for measuring a sample, and a detector for detecting a sample;

the drive circuit is configured so as to drive at least one of the first actuator, second actuator, and detector according to the control data.

6. The sample processing apparatus according to claim 1, wherein the sample processing unit further comprises a memory for storing the control data received by the first communication part; and the drive circuit is configured so as to drive the operating device according to the control data which is stored in the memory of the sample processing unit.

7. The sample processing apparatus according to claim 1, wherein the operating unit is controlled by the control data without a processor.

8. The sample processing apparatus according to claim 1, wherein the processor executes a process for generating the control data at intervals of less than or equal to an average of approximately 100 msec.

9. The sample processing apparatus according to claim 1, wherein the first communication part and second communication part comprise a USB interface.

10. The sample processing apparatus according to claim 1, wherein the operating device comprises a measuring device for measuring a sample and generating measurement data;

the first communication part is configured so as to transmit the measurement data generated by the measuring device to the second communication part; and the second communication part is configured so as to receive the measurement data transmitted from the first communication part;

the processor processes the measurement data received from the second communication part, and obtains a sample analysis result.

11. The sample processing apparatus according to claim 10, wherein the operating device is configured so as to measure blood as a sample; and the processor is configured so as to obtain a number of blood cells as the analysis result.

12. The sample processing apparatus of claim 1, wherein the sample processing unit includes:

a memory storing a first program for generating the control data;

a second program for processing the data output from the sample processing unit; and an operating system which determines priority of program execution;

wherein the first program and the second program are stored in the memory such that the first program is executed by interrupting execution of the second program under control of the operating system.

13. The sample processing apparatus of claim 1, wherein the control data includes an amount of movement and a timing of the movement of the operating device.

14. A data processing apparatus, comprising:

a memory for storing an operating system and a control program for controlling an operating device of a sample processing apparatus for processing a sample; wherein the control program is stored in the memory and is executable at a kernel level of the operating system;

a processor for executing a control program stored in the memory, and generating, at fixed time intervals, control data defining a content of an operation by the operating device; and a communication part which is connected so as to be capable of communication with the sample processing apparatus, for transmitting the control data generated by the processor to the sample processing apparatus.

15. The data processing apparatus according to claim 14, wherein the communication part is configured so as to transmit the control data to the sample processing apparatus by interrupt transfer.

16. The data processing apparatus according to claim 14, wherein the memory further stores a data processing program for processing data output from the sample processing apparatus;

the data processing program is stored in the memory and is executable at an user level of the operating system.

17. The data processing apparatus according to claim 14, wherein the communication part comprises a USB interface.

18. A sample processing apparatus, comprising:

a sample processing unit for processing a sample; and a data processing unit for processing data output from the sample processing unit, wherein the sample processing unit includes a memory under control of a processor, the memory storing a first program for generating, at fixed time intervals, control data defining a content of an operation by the sample processing unit, a second program for processing the data output from the sample processing unit, and an operating system which determines priority of program execution, wherein the first program and the second program are stored in the memory such that the first program is executed by interrupting execution of the second program under control of the operating system.

19. The sample processing apparatus according to claim 18, wherein the first program is stored in the memory and is executable at a kernel level of the operating system.

20. The sample processing apparatus according to claim 19, wherein the second program is stored in the memory and is executable at an user level of the operating system.

* * * * *

UNITED STATES PATENT AND TRADEMARK OFFICE
CERTIFICATE OF CORRECTION

| | |
|---|---|
| PATENT NO. | : 8,131,382 B2 |
| APPLICATION NO. | : 12/286031 |
| DATED | : March 6, 2012 |
| INVENTOR(S) | : Shoichiro Asada |

It is certified that error appears in the above-identified patent and that said Letters Patent is hereby corrected as shown below:

In the Claims

In column 11, claim 4, line 26, after "according to" replace "claim," with --claim 3,--.

Signed and Sealed this
Fourth Day of September, 2012

David J. Kappos
*Director of the United States Patent and Trademark Office*